United States Patent [19]

Lu et al.

[11] Patent Number: 5,782,881
[45] Date of Patent: Jul. 21, 1998

[54] PACEMAKER WITH SAFETY PACING

[76] Inventors: Richard Lu, 9917 S. Spring Hill Ln., Highlands Ranch, Colo. 80126; Tibor Nappholz, 8524 E. Jamison Ave., Englewood, Colo. 80112

[21] Appl. No.: 717,305

[22] Filed: Sep. 20, 1996

[51] Int. Cl.⁶ .................................................. A61N 1/30
[52] U.S. Cl. ............................................................ 607/9
[58] Field of Search ....................................... 607/9, 14, 17

[56] References Cited

U.S. PATENT DOCUMENTS 4,552,154  11/1985  Hardaub ........................... 128/702
4,702,253  10/1987  Nappholz et al. .
4,766,901  8/1988   Callaghan .
4,901,725  2/1990   Nappholz et al. .
5,441,523  8/1995   Nappholz .

Primary Examiner—Scott M. Getzow
Attorney, Agent, or Firm—Gottlieb, Rackman & Reisman

[57] ABSTRACT

In a cardiac pacemaker, a monitoring window is defined during the a-v delay during which signals sensed in the ventricular channel are monitored. If an abnormal signal is sensed during this window, certain features of this signal are analyzed to determine its origin, such as PVC. If the signal cannot be categorized as a known signal, a safety pacing pulse is applied.

14 Claims, 8 Drawing Sheets

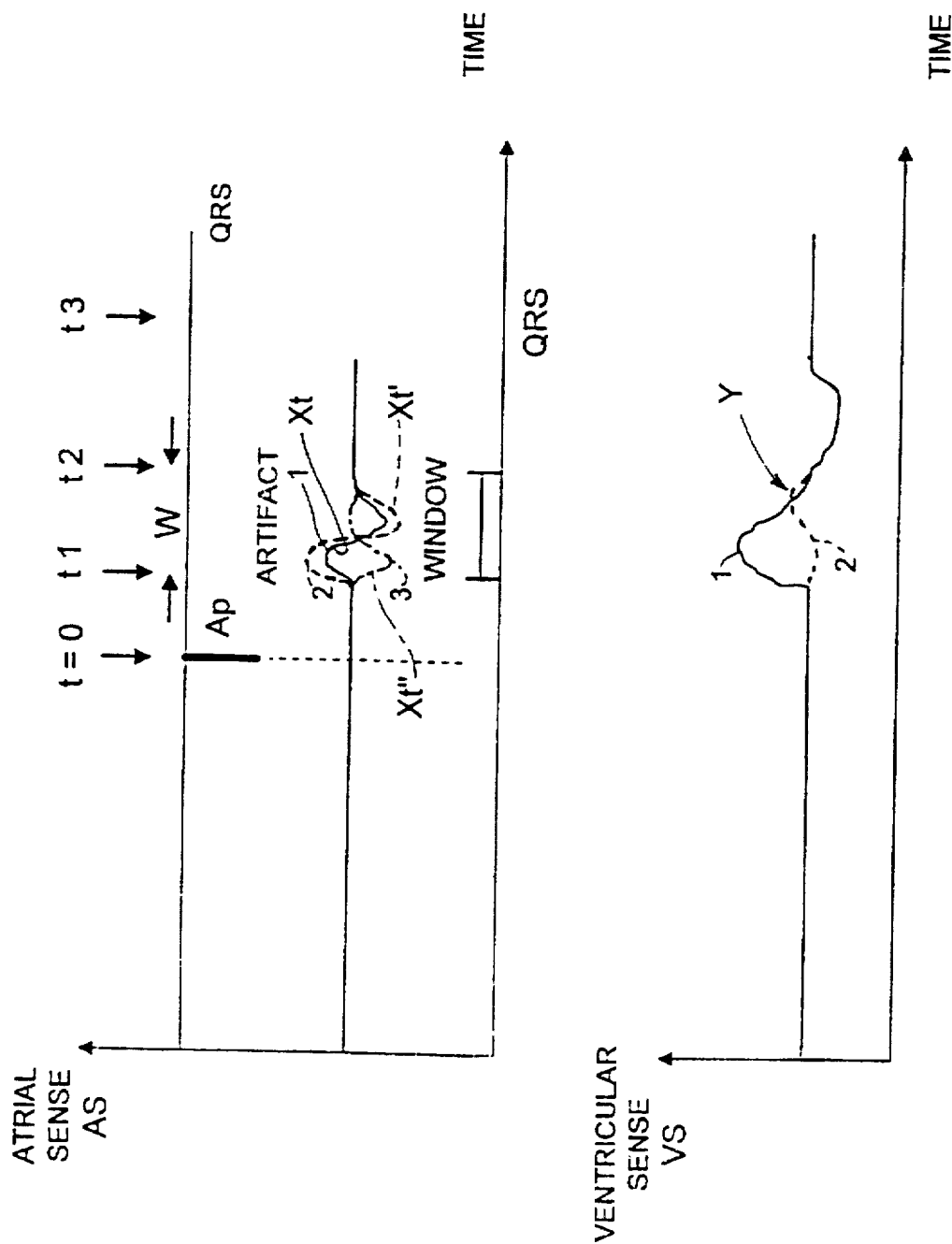

PACEMAKER WITH SAFETY PACING

BACKGROUND OF THE INVENTION

1. Field of the Invention

This invention relates to single or dual chamber pacemakers, and more particularly to a mode of operation wherein intrinsic cardiac activity in a cardiac chambers is monitored and if no intrinsic activity is sensed then, after a preset duration, the chamber is paced. Importantly, a monitoring window is defined to detect cross channel artefacts, thereby increasing the sensitivity and responsiveness of the system.

2. Description of the Prior Art

Conventional pacemakers operating, for example, in a DDDX mode are normally provided with means for sensing and pacing both the atrium and the ventricle. Typically in these types of devices, if an intrinsic or pacing pulse occurs in one of the chambers, for example the atrium, then this activity may be erroneously sensed in the other chamber due to cross talk. In order to eliminate this type of error, in the past, pacemakers have been provided with blanking periods for blanking the sensor in one channel after pacing pulse occurs in the other. This blanking period is usually referred to as the cross-channel blanking period. (Pacemakers may also be provided with in-channel blanking periods, which are of no interest to the present invention.) Following the blanking period an alert period is normally designated during which the cardiac chamber of interest is monitored for intrinsic activity. If no such activity is sensed by the end of this alert period than a pacing pulse is applied to the chamber. One such pacemaker is described in commonly assigned U.S. Pat. No. 5,441,523, and incorporated herein by reference.

However a problem with the pacemakers described above has been selecting the duration of the blanking period for a particular channel properly. If the blanking period is too short, a cross-channel artefact could be interpreted as an intrinsic activity and therefore pacing may be erroneously inhibited. On the other hand, if the blanking period is too long, an intrinsic activity may be missed and the chamber may be paced when no such pacing is required. Either situation is undesirable physiologically. In addition, generating excessive pacing pulses is wasteful because it reduces the life of the pacemaker battery.

OBJECTIVES AND SUMMARY OF THE INVENTION

In view of the disadvantages of the prior art, it is an objective of the present invention to provide a pacemaker in which cross channel blanking is substantially reduced to a very short duration to avoid missed intrinsic cardiac activity.

A further objective is to provide a pacemaker with means for recognizing and discriminating a cross channel artefact from an intrinsic cardiac activity on a cardiac chambers.

Another objective is to provide a pacemaker in which safety pulses can be applied with confidence because cross-channel artefacts are recognized and distinguished from intrinsic activity.

Other objectives and advantages of the invention shall become apparent form the following description. Briefly, a pacemaker constructed in accordance with this invention includes means for sensing intrinsic activity in the atrium and ventricle, means for generating pacing pulses for the atrium and ventricle and microprocessor means for analyzing the signals sensed in the atrium and ventricle and for generating corresponding control signals. These control signals are used to drive a state machine which in response generates pacing commands, as required. Importantly, the pacemaker further includes means for determining if an activity sensed in a cardiac chamber is intrinsic or due to cross channel activity or noise. Cross channel activity is ignored. If intrinsic cardiac activity is identified, no pacing pulse is applied. If no decision can be made as to the source of cardiac activity then a safety pacing pulse is applied.

Preferably cross channel activity is recognized from certain waveform features extracted during a critical window. Information defining cross-channel activity may be averaged over several cardiac cycles to define a template.

BRIEF DESCRIPTION OF THE DRAWINGS

Further objects, features and advantages of the invention will become apparent upon consideration of the following description, taken in conjunction with the accompanying drawings, in which:

FIG. 5 shows a graph indicating an atrial pulse, and the corresponding cross channel activity;

FIG. 6 shows a ventricular signal consisting of an atrial cross channel pulse and a preliminary ventricular contraction.

DETAILED DESCRIPTION OF THE INVENTION

Figure 1:
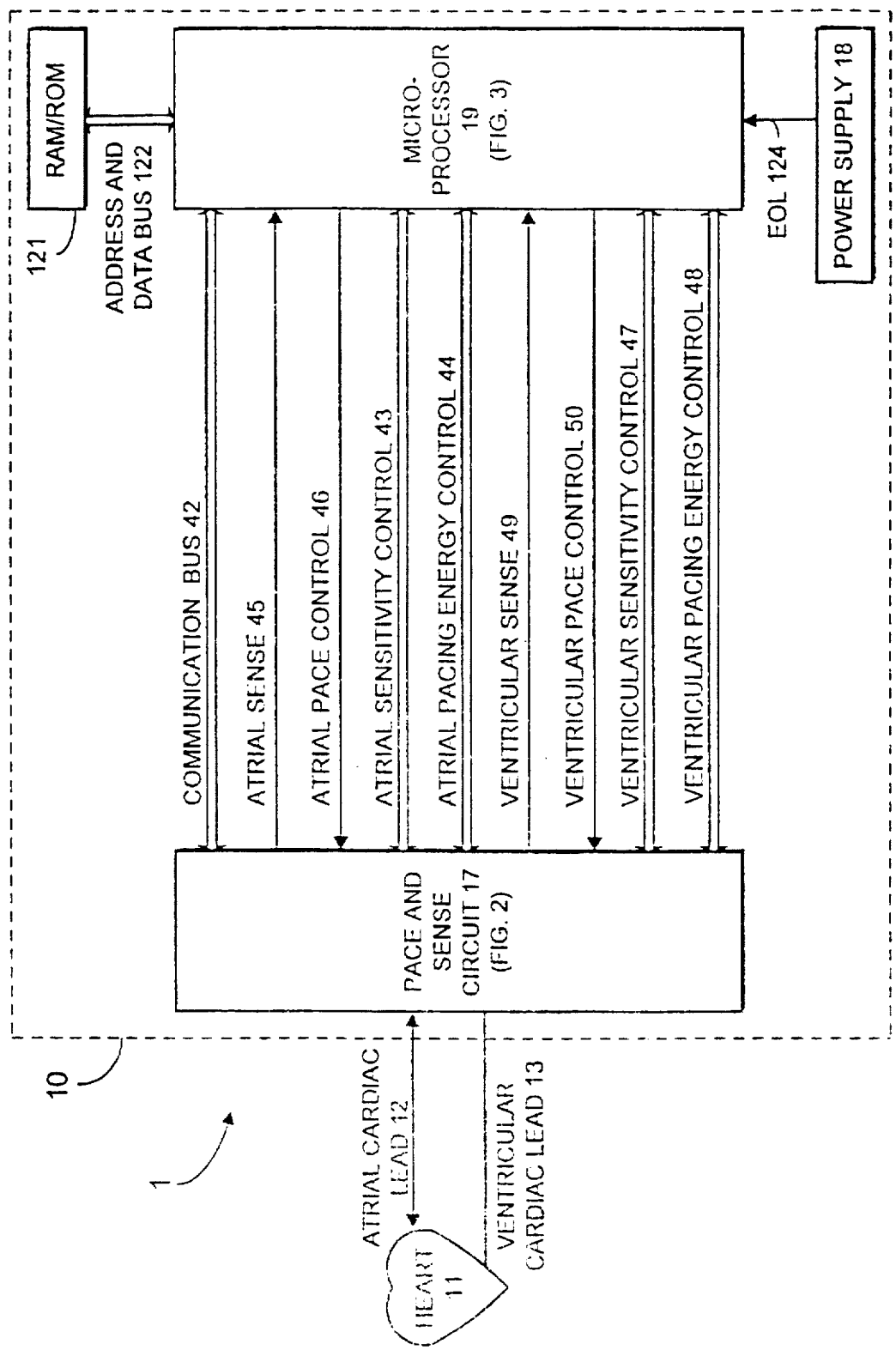
FIG. 1 is a block diagram of a rate-responsive, dual chamber pacemaker which embodies the subject invention.

FIG. 1 shows a block diagram of a pacemaker 1. The pacemaker 1 is designed to be implanted in a patient and includes a pulse generator 10 and appropriate leads for electrically connecting the pulse generator to a patient's heart 11. The pacemaker includes an atrial cardiac lead 12 extending to the atrium of the patient's heart for the administration of pacing therapy to the atrium, and a ventricular cardiac lead 13 extending to the ventricle of the patient's heart for the administration of pacing therapy to the ventricle. The pulse generator 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a reliable voltage level to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of the approach of battery failure in the power supply 18. The microprocessor 19 and the pace and sense circuit 17 are connected by a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
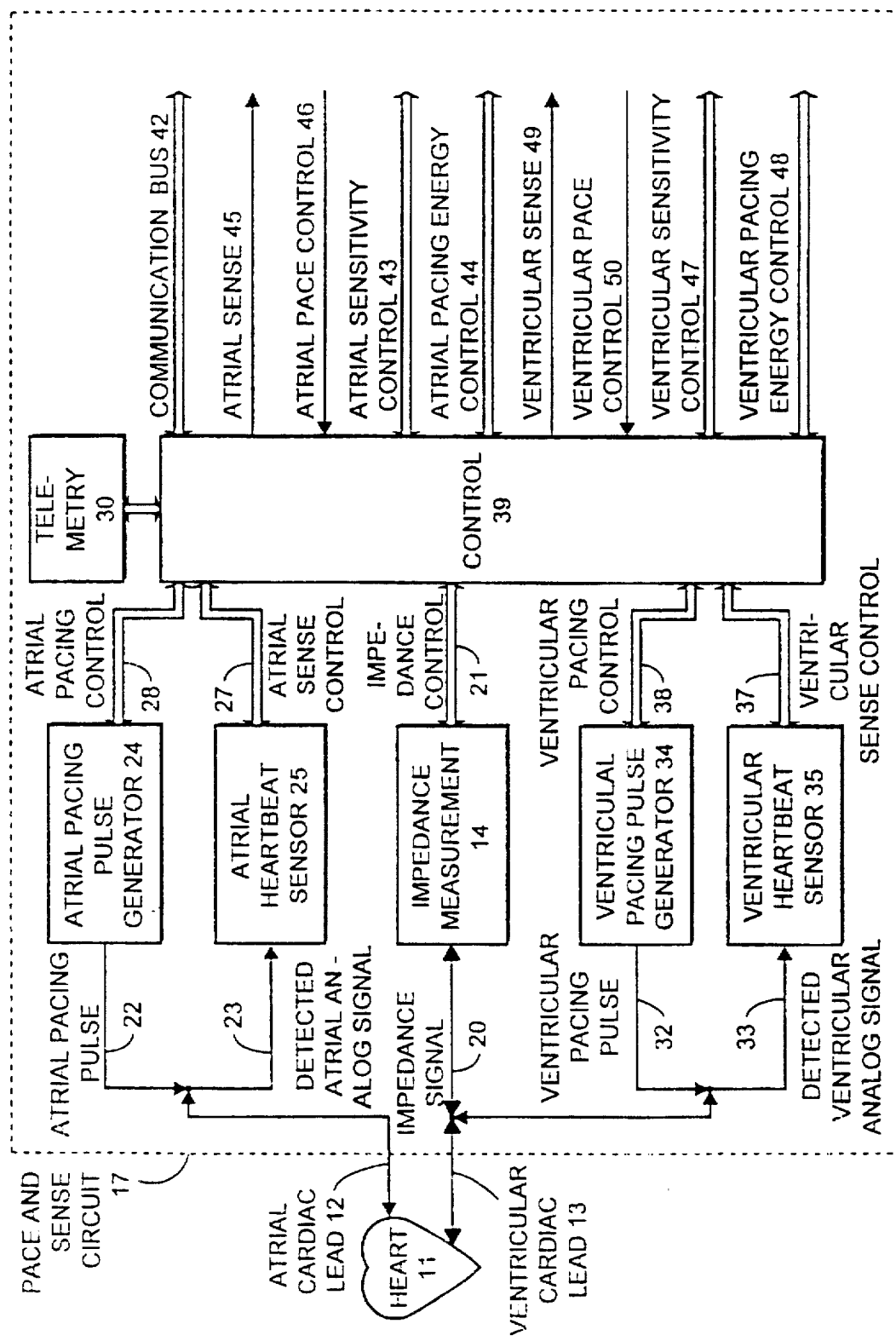
FIG. 2 is a block diagram of the pace and sense circuit 17 of FIG. 1.

FIG. 2 shows the pace and sense circuit 17 which includes circuitry for an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 includes an impedance measurement circuit 14 for measuring a physiological parameter indicative of the patient's metabolic demand. Also, the pace and sense circuit 17 includes a control block 39 which has an interface to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control 27 and an input ventricular sense control 37, respectively, from the control block 39 which determines the sensitivities of the sensor circuits. The sensitivity determines the minimum voltage deviation required at a sensing electrode for a sense to be registered, i.e., a depolarization signal to be recognized by the pacemaker.

The atrial pacing pulse generator circuit 24 receives from the control block 39, via an atrial pacing control bus 28, an atrial pace control input and an atrial pacing energy control input to generate an atrial pacing pulse 22 at appropriate times. Similarly, the ventricular pacing pulse generator circuit 34 receives from the control block 39, via a ventricular pacing control bus 38, a ventricular pace control input and a ventricular pacing energy control input to generate a ventricular pacing pulse 32. The atrial and ventricular pace control inputs determine the respective types of atrial and ventricular pacing that take place, while the atrial and ventricular pacing energy control inputs determine the respective magnitudes of the pulse energies.

The pacemaker 1 makes an impedance measurement when the microprocessor 19 sends a signal on the impedance control bus 21 to activate the impedance measurement circuit 14. The impedance measurement circuit 14 then applies a current to the ventricular cardiac lead 13 and measures a voltage resulting from the applied current to monitor the impedance. The current and voltage signals jointly are termed an impedance signal 20.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 3:
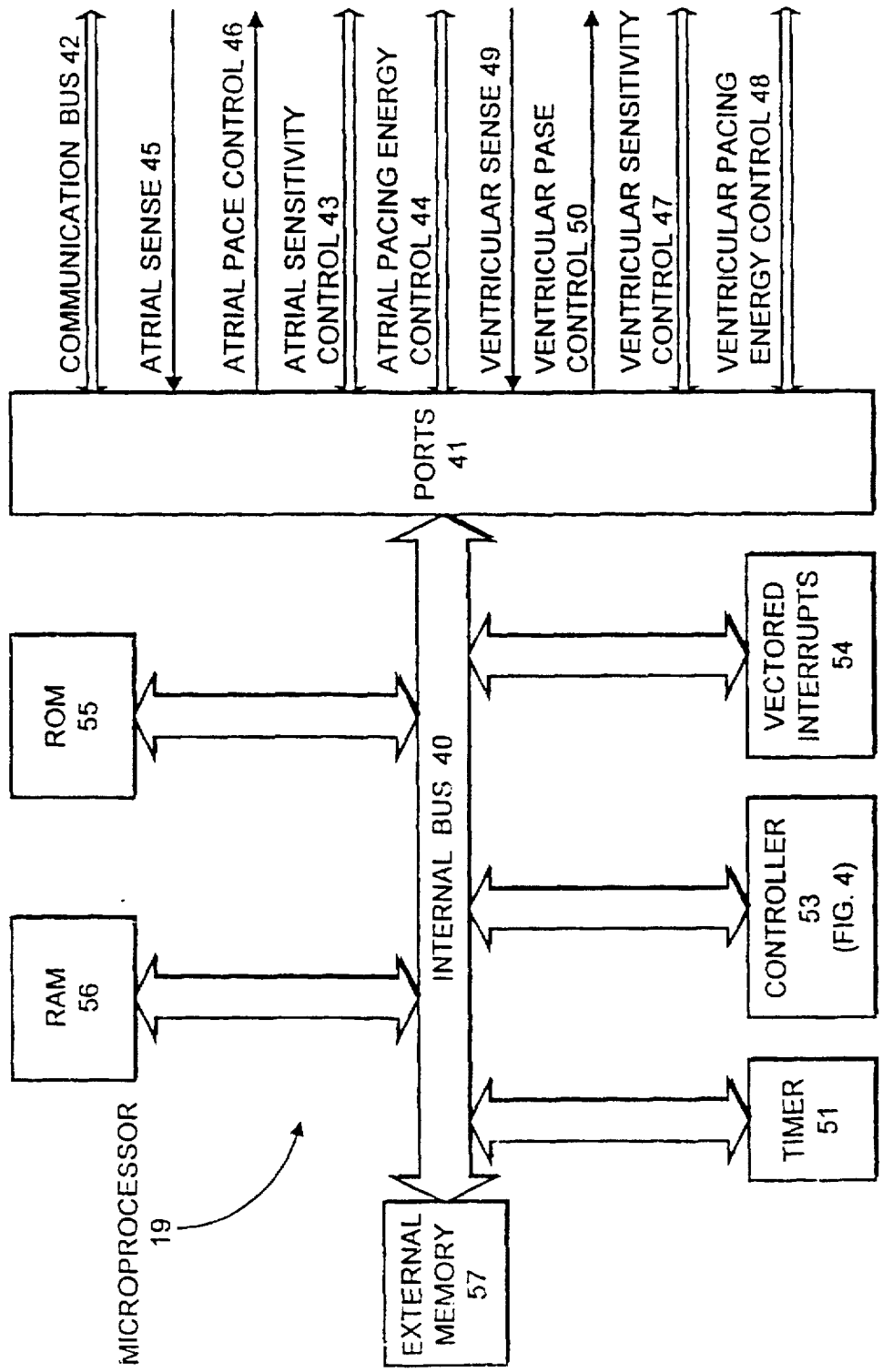
FIG. 3 is a block diagram of the microprocessor of FIG. 1.

FIG. 3 shows the microprocessor 19 as comprising a timer circuit 51 which may include multiple individual 16-bit timer circuits, a controller 53, a vectored interrupts block 54, a ROM 55, a RAM 56, an external memory 57 and a ports block 41. These circuits mutually communicate using an internal communications bus 40. The timer 51 may include several individual circuits or may include one or more timer circuits with a single timer performing multiple function timing operations under direction of software running on the controller 53 for generating various timing signals as discussed below. The RAM 56 acts as a scratchpad and active memory during execution of the programs stored in the ROM 55 and used by the microprocessor 19. These programs include system supervisory programs, detection algorithms for detecting and confirming arrhythmias, and programming for implementing the logic diagram of FIGS. 12, 13, 14 and 15, as well as storage programs for storing, in external memory 57, data concerning the functioning of the pulse generator 10 and the electrogram provided by the ventricular cardiac lead 13. The timers 51, and their associated control software, implement some timing functions required by the microprocessor 19 without resort entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communications bus 42 serves to provide signals indicative of such control to the microprocessor 19.

Appropriate telemetry commands will cause the telemetry circuit 30 to transmit data to the external programmer. Data stored is read out, by the microprocessor 19, on to the communications bus 42, through the control block 39 in the pace and sense circuit 17, and into the telemetry circuit 30 for transmission to the external programmer by a transmitter in the telemetry circuit 30.

The microprocessor 19 through its ports block 41 receives status and/or control inputs from the pace and sense circuit 17, such as the sense signals on the sense lines 45 and 49. It performs operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits.

The pacemaker 1 may employ a metabolic sensor to distinguish whether atrial heartbeats are occurring at a physiological rate or a pathological rate. The pacemaker 1 responds to a physiological atrial rate by functioning in an AV synchronous pacing mode with pacing pulses in the ventricle delivered a predetermined interval following an atrial heartbeat. When the pacemaker 1 detects a pathological atrial rate, it responds by functioning in the forced synchrony mode of operation. A metabolic sensor system, which is suitable for operation in the present invention, may be made up of one or more known sensors either solely or in combination with other sensors, including but not limited to minute volume, ventricular depolarization gradient, QT-interval, oxygen saturation, Ph, central venous blood temperature, right ventricular pressure, stroke volume, systolic time intervals, respiration rate and ultrasonic or pressure monitoring of cardiac output. The pacemaker 1 of the present invention will function properly using any metabolic indicator rate system, so long as that system is able to reliably relate the sensed parameter to a metabolic demand pacing rate. U.S. Pat. No. 4,766,901, to F. Callaghan, issued Aug. 30, 1988, for "Rate Responsive Pacing System Using the Integrated Evoked Potential," refers to the operation of a rate-responsive pacing system using an integrated evoked ventricle depolarization potential as a metabolic demand pacing rate indicator. U.S. Pat. No. 4,702,253 to T. Nappholz et al., issued Oct. 27, 1987, for "Metabolic-Demand Pacemaker and Method of Using the Same to Determine Minute Volume," and U.S. Pat. No. 4,901,725, to T. Nappholz et al., issued Feb. 20, 1990 for "Minute Volume Rate-Responsive Pacemaker", disclose rate-responsive pacers describing another metabolic demand pacing rate indicator, respiratory minute volume, as the rate control parameter. The above-mentioned patents are hereby incorporated by reference. The preferred embodiment of the invention employs an impedance sensor 14, shown in FIG. 2 which may perform the respiratory minute volume measurements of the Nappholz et al. patents.

Figure 4:
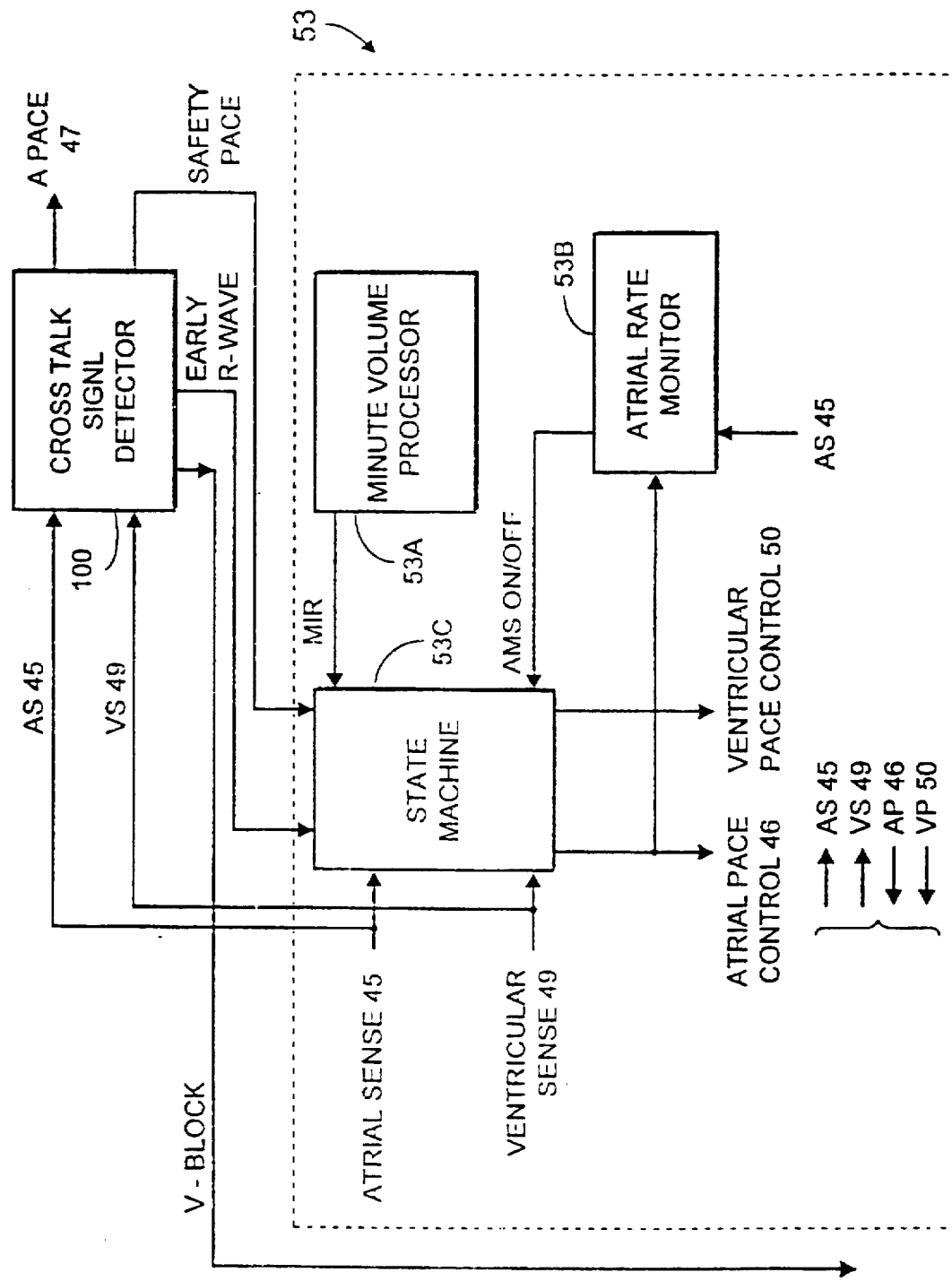
FIG. 4 is a functional block diagram of the controller of FIG. 3.

FIG. 4 shows the functional block diagram of the controller 53 of FIG. 3. The minute volume processor 53A uses the data supplied via the internal bus 40 and the communication bus 42 from the impedance measurement block 14 to generate the Metabolic Indicated Rate Interval [MIR] which is used by the pacing and sensing system (shown symbolically as the "DDD pacer block 53C in FIG. 4) to determine the length of each of the intervals used in the timing cycle. The atrial rate monitor 53B, generates an AMS signal which will be described at length below. FIG. 4 depicts the signals which control several of the operations involved in the forced synchrony sequencing. The operation of the pacemaker described so far is disclosed in detail in U.S. Pat. No. 5,441,523, incorporated herein by reference.

Importantly, the subject pacemaker further includes a cross talk determinator 100 shown in FIG. 4. In order to understand the operation of this circuit, reference is now made to FIG. 5, 6, 8A and 8B showing typical atrial signals sensed on an AS line 45 and typical ventricular signals sensed on a VS line 49. As seen in this Figure, at a particular time t=0 an atrial pace Ap is applied. Following this pace, at time t1 a cross talk signal Xt is detected in the VS line. Signal Xt may last about 35–40 msec, until t2. In a typical prior art pacemaker, the signal Xt is not detected because it occurs during a cross channel blanking period. Following signal Xt, at time t3, an intrinsic QRS complex occurs in the ventricle and is sensed on line VS as shown. The objective of the present invention is to recognize the cross talk signal Xt and differentiate it from the QRS complex.

Importantly, the Xt signal has a number of well defined characteristics. First, time period for its onset is in the range of 30–35 msec. This parameter is dependent on the physiology of the patient as well as the electrical characteristics and physical characteristics of the atrial and ventricular leads, the method of fixation used to secure the leads into the heart, and so on. Time period t1 may be determined initially during implantation. Second, while over time, the peak amplitude and polarity of the Xt signal may change slightly, as illustrate for example by signals Xt' and Xt", it will invariably exhibit two peak values of opposite polarities within a time period W defined between t2, t1.

However, during W, a QRS complex due to a preliminary intrinsic ventricular contraction (PVC) may occur which may be superimposed on the Xt signal. The resulting signal Y is shown in FIG. 6. This signal Y clearly has only one peak or maximum value.

Thus, the features of the signals detected on line VS between t1 and t2 can be analyzed and used to confirm either a cross talk signal Xt, a premature QRS complex, or alternatively, an unidentified signal in which case, safety pacing should be applied.

Figure 7A:
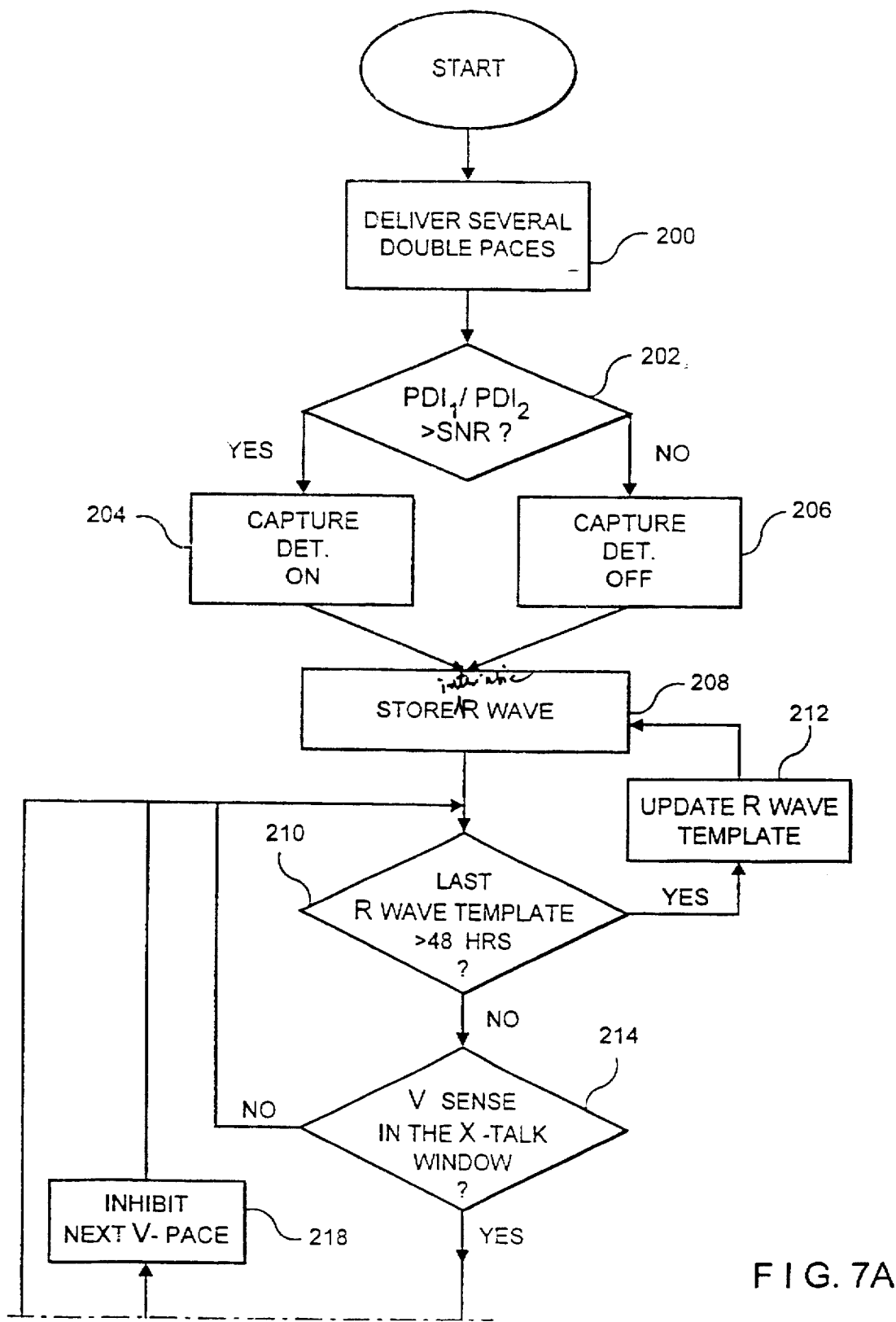
FIGS. 7a and 7b shows a flow chart for the operation of the cross channel signal detector of FIG. 4.
Figure 7B:
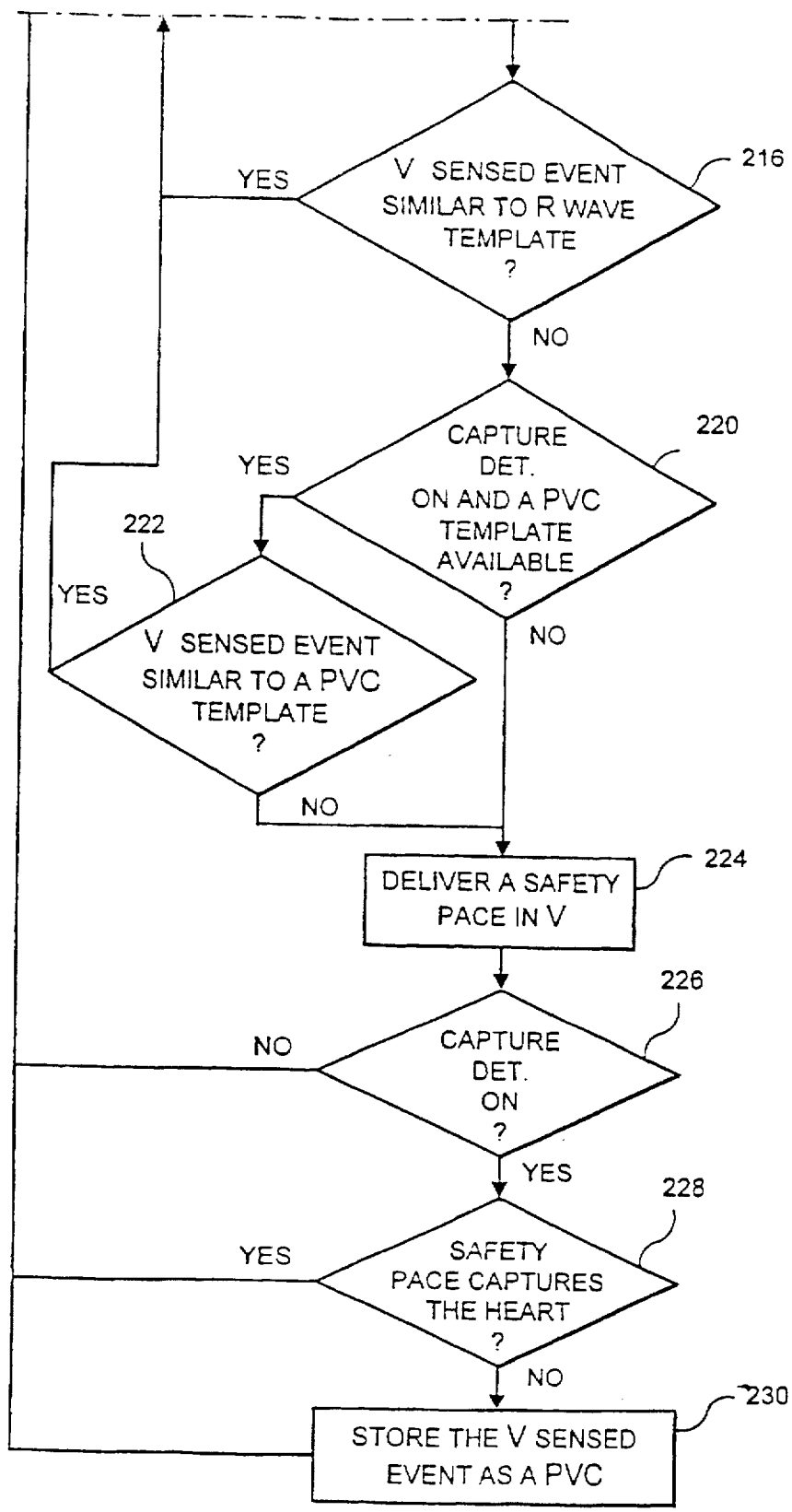
Figure 8A:
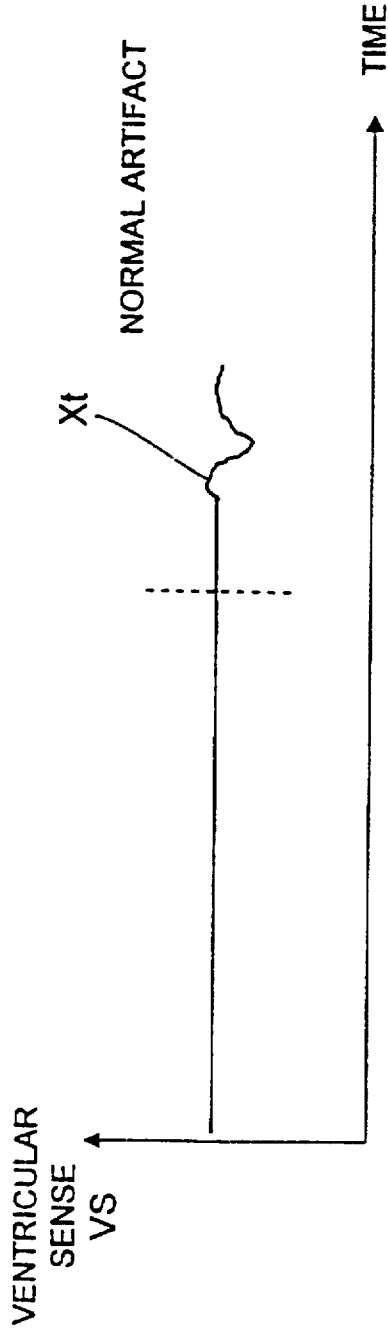
FIG. 8A shows a normal artifact sensed in the ventricle.
Figure 8B:
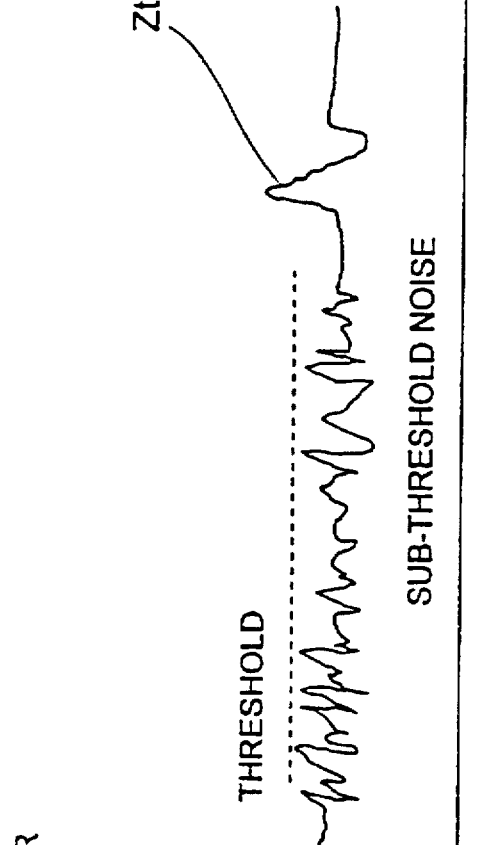
FIG. 8B shows an artifact present in the ventricle with noise.

The operation of a pacemaker with the inventive feature of the present invention is now described in conjunction with the flow chart of FIGS. 7a and 7b. Initially, in step 200, several atrial pairs of pacing pulses are delivered. The pulses of each pair are separated by a time, selected to be smaller than the normal A-V delay. In step 202 the PDI (paced depolarization integral) corresponding to each pacing pulse is measured and the ratio of these parameters is compared to a signal-to-to-noise ratio SNR. Typical SNR is set to 8:1. If the ratio of the first PDI (PDI1) to the second (PDI2) is greater than SNR for at least most of the pacing pairs than it is assumed that the patient's heart has been captured, and in step 204 a flag is set to indicate capture detection. For example, in step 202, a "yes" determination may be made if for m out of n consecutive pairs, DDI1/PDI2>SNR, where m and n may be five and seven. An apparatus for measuring PDI is formed in U.S. Pat. No. 5,184,615. If this ratio is smaller than SNR than the flag for capture detection is set off in step 206.

Following each pacing pair, the ventricular sense line VS49 is monitored after the A-V delay to detect intrinsic R-waves responsive to a pacing pulse AP. When this R-wave is detected, in step 208 it is stored.

In step 210 the time for an R-wave template stored previously is checked. If the R-wave template is over 48 hours old than in step 212 the R-wave obtained in step 208 is stored as the latest or update R-wave template.

In step 214, the window W is defined between t=t1 and t=t2 and this window is monitored. If no signal is detected in this window W, then normal pacing continues.

If a signal is detected during this window W then in step 216 this signal is compared with the intrinsic R-wave template previously stored. If the signal detected during the window W appears to be similar to the intrinsic R-wave then it is assumed that this signal is an early intrinsic wave. Therefore in step 218 the next ventricular pace is inhibited.

If in step 216 the sensed signal is determined not to be similar to the intrinsic R-wave template, then in step 220 the capture detection flag is tested. Another test performed in step 220 is whether a PVC template is available from previous occurrences. If the capture flag is on and a PVC template is available, then in step 222 the sensed signal is compared to the PVC template. If in step 222 a match is detected than the signal detected in the window is due to PVC. Therefore in step 218 the next ventricular pace signal is inhibited, as discussed above, and normal pacing continues. If the conditions of step 220 or step 222 are not met than in step 224 a safety pace signal is delivered to the ventricle.

Following the safety pace signal of step 224, another test is performed in step 226 to determine if the capture detection flag is on. If the capture flag is off, normal pacing resumes. If the capture flag is on then in step 228 a test is performed to determine if the safety pace signal has captured the heart. If it has not then normal pacing continues, if it has, then in step 230 the signal detected in the window W is stored is a PVC template.

The operation described in the flow chart of FIGS. 7A and 7B is performed by the detector 100 in FIG. 4. The detection senses signals from the ventricle on line VS49, and atrial signals on line AS45. The detector 100 also generates atrial pace signals on line AP47, as described in conjunction with FIG. 8. If a signal sensed on VS49 during window W is identified as a crosstalk signal Xt, then it is ignored. If it is identified as a PVC, then an early R-wave signal is sent to the state machine 53C, which in response means that the next V-pace signal is suppressed. If an unknown signal is detected in window W then a SAFETY PACE signal is sent to the state machine which in response issues a safety V-pace command on line VP50.

The invention was described above for recognizing cross talk from the atrial chamber to the ventricle during atrial events. However, the invention may similarly be applied for detecting and correcting for cross talk from the ventricle to the atrium during ventricular events (normally referred to as 'back chat').

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claimed:

1. A dual chamber pacemaker comprising:

atrial pacing means for generating atrial pacing pulses for the atrium;

ventricular sensing means for sensing activity in the ventricle;

ventricular pacing means for generating ventricular pacing pulses for the ventricle;

a-v interval means for defining an a-v interval between atrial and ventricle activities;

monitoring means for defining a monitoring window within said a-v delay and for detecting an abnormal signal during said monitoring window;

feature extracting means for extracting features of said abnormal signal;

categorizing means for categorizing said abnormal signal as one of a plurality of preselected signals based on said features; and safety pacing means for generating a ventricular signal if said categorizing means does not categorize said abnormal signal.

2. The pacemaker of claim 1 wherein said categorizing means categorizes said abnormal signal as a PVC or intrinsic R-wave.

3. The pacemaker of claim 1 further comprising capture means for detecting if said atrial pacing pulses capture the heart.

4. The pacemaker of claim 3 wherein said ventricular safety pacing pulse is generated if said heart is captured.

5. The pacemaker of claim 1 further comprising a template generator for generating a template for one of an atrial and a ventricular intrinsic pulse, said categorizing means using said template to categorized said abnormal signal.

6. The pacemaker of claim 5 further comprising a timer, said timer generating a control signal to update said template at preselected time intervals.

7. The pacemaker of claim 1 wherein said monitoring means monitors intrinsic signals sensed in the ventricle.

8. In a dual chamber pacemaker wherein an a-v interval is defined between atrial and ventricular events, a method of generating a ventricular safety pacing pulse comprising the steps of:

defining a window within said a-v interval;

monitoring during said window the ventricular chamber for an abnormal signal;

classifying said abnormal signal, when detected, as one of a preselected signals; and generating said ventricular safety pacing signal if said ventricular signal cannot be classified during said classifying step.

9. The method of claim 8 further comprising the step of determining if said atrial pacing pulses capture the heart.

10. The method of claim 9 wherein said safety pacing pulse is generated in the absence of capture.

11. The method of claim 8 further comprising generating templates for intrinsic ventricular events.

12. The method of claim 11 wherein said step of generating includes generating R-wave templates characteristic of R-waves.

13. The method of claim 12 wherein said step of generating includes generating PVC templates characteristic of premature ventricular contractions.

14. The method of claim 11 wherein said step of classifying includes comparing said templates to said abnormal signal.

* * * * *